United States Patent
Kleinszig et al.

(10) Patent No.: US 10,022,098 B2
(45) Date of Patent: *Jul. 17, 2018

(54) METHOD AND DEVICE FOR GENERATING A LOW-DOSE X-RAY IMAGE PREVIEW, IMAGING SYSTEM AND COMPUTER PROGRAM PRODUCT

(71) Applicants: SIEMENS AKTIENGESELLSCHAFT, Munich (DE); THE JOHNS HOPKINS UNIVERSITY, Baltimore, MD (US)

(72) Inventors: Gerhard Kleinszig, Forchheim (DE); Jeffrey Siewerdsen, Baltimore, MD (US); Sebastian Vogt, Monument, CO (US); Adam Wang, Baltimore, MD (US)

(73) Assignees: Siemens Aktiengesellschaft, Munich (DE); The Johns Hopkins University, Baltimore, MD (US)

( * ) Notice: Subject to any disclaimer, the term of this patent is extended or adjusted under 35 U.S.C. 154(b) by 396 days.

This patent is subject to a terminal disclaimer.

(21) Appl. No.: 14/795,206

(22) Filed: Jul. 9, 2015

(65) Prior Publication Data
US 2016/0007946 A1  Jan. 14, 2016

Related U.S. Application Data

(60) Provisional application No. 62/022,548, filed on Jul. 9, 2014.

(51) Int. Cl.
*A61B 6/14* (2006.01)
*A61B 6/00* (2006.01)
*A61B 6/03* (2006.01)

(52) U.S. Cl.
CPC .......... *A61B 6/5205* (2013.01); *A61B 6/032* (2013.01); *A61B 6/4085* (2013.01); *A61B 6/488* (2013.01); *A61B 6/542* (2013.01); *A61B 6/5258* (2013.01)

(58) Field of Classification Search
CPC ....... A61B 6/488; A61B 6/5258; A61B 6/542; A61B 6/02; A61B 6/4233; A61B 6/461;
(Continued)

(56) References Cited

U.S. PATENT DOCUMENTS

| | | | |
|---|---|---|---|
| 2012/0155609 A1* | 6/2012 | Lemminger | A61B 6/032 378/62 |
| 2013/0108130 A1* | 5/2013 | Nukui | A61B 6/488 382/131 |
| 2013/0148782 A1* | 6/2013 | Tajima | A61B 6/542 378/62 |

FOREIGN PATENT DOCUMENTS

EP  1444952 B1 *  5/2008  ............... A61B 6/06

OTHER PUBLICATIONS

A. Uneri et al., "3D-2D registration for surgical guidance: Effect of projection view angles on registration accuracy," Physics in Medicine and Biology vol. 59 (2014) pp. 271-287.
(Continued)

*Primary Examiner* — Irakli Kiknadze
(74) *Attorney, Agent, or Firm* — Laurence Greenberg; Werner Stemer; Ralph Locher (57) ABSTRACT

A method of generating a preview of at least one low-dose x-ray image includes the followings steps: obtaining an initial volumetric representation of a patient from an x-ray device; creating at least one x-ray image projection from the initial volumetric representation; injecting correlated noise into at least one of the x-ray image projections; and processing the noise-injected x-ray image projections to create at least one preview of a patient-specific low-dose x-ray for
(Continued)

showing to a user. There are also described a device for generating at least one preview of a low-dose x-ray image, a corresponding imaging system, and a non-transitory computer readable medium.

15 Claims, 7 Drawing Sheets

(58) Field of Classification Search
CPC ........... A61B 6/582; A61B 6/03; A61B 6/032; A61B 6/4085; A61B 6/52; A61B 6/5205; A61B 6/5211; A61B 6/5282; A61B 6/545; A61B 6/482; A61B 6/5235; A61B 6/583; A61B 6/4283; A61B 6/4216; A61B 6/585; A61B 6/4035; A61B 6/466; A61B 6/469; A61B 6/4291; A61B 6/05; G06T 7/0012; G06T 11/008; G06T 5/50; G06T 2207/10081; G06T 2207/30028; G06T 2207/30; G06F 3/1236; H04N 1/32117; H04N 2201/3208
USPC .................................................. 378/4, 19, 62
See application file for complete search history.

(56) References Cited

OTHER PUBLICATIONS

M. Söderberg et al."Simulated dose reduction by adding artificial noise to measured raw data: a validation study" Radiation Protection Dosimetry, Feb. 19, 2010, pp. 1-7.
J. Wang et al., "Dose reduction for kilovotage cone-beam computed tomography in radiation therapy," Physics in Medicine and Biology, vol. 53 (2008) pp. 2897-2909.
A. S. Wang et al., "Patient-specific minimum-dose imaging protocols for statistical image reconstruction in C-arm cone-beam CT using correlated noise injection," in SPIE Medical Imaging, 2014, p. 90331P-1.
R. Fahrig et al., "Use of a C-Arm System to Generate True Three-dimensional Computed Rotational Angiograms: Preliminary In Vitro and In Vivo Results", AJNR Am J Neuroradiol 18, Sep. 1997, pp. 1507-1514.
R. E. Van Gelder et al., "CT Colonography at Different Radiation Dose Levels: Feasibility of Dose Reduction," Radiology, vol. 224, No. 1, pp. 25-33, 2002.
A. J. Britten et al., "The addition of computer simulated noise to investigate radiation dose and image quality in images with spatial correlation of statistical noise: an example application to X-ray CT of the brain," British Journal of Radiology, vol. 77, (2004), pp. 323-328.
Y. Long et al., "3D forward and back-projection for X-ray CT using separable footprints," Medical Imaging, IEEE Transactions, Nov. 2010 vol. 29, No. 11, pp. 1839-1850.
H. Erdogan et al.,"Ordered subsets algorithms for transmission tomography," Physics in Medicine and Biology, vol. 44, (1999), pp. 2835-2851.
A. S. Wang et al., "Low-Dose Preview for Patient-Specific, Task-Specific Technique Selection in Cone-Beam CT," Medical Physics, vol. 41, No. 7, p. 071915, 2014.
D. J. Tward et al., "Cascaded systems analysis of the 3D noise transfer characteristics of flat-panel cone-beam CT," Medical Physics, vol. 35, No. 12, Dec. 2008 p. 5510.
N. Navab et al., "Dynamic geometrical calibration for 3D cerebral angiography," In Proceedings of SPIE, 1996, vol. 2708, p. 361.
M. J. Daly et al., "Geometric calibration of a mobile C-arm for intraoperative cone-beam CT," Medical physics, 35, (5), May 2008 p. 2124.
J. W. Stayman et al., "Overcoming nonlinear partial volume effects in known-component reconstruction of Cochlear implants," in SPIE Medical Imaging, 2013, p. 86681L.

T. M. Benson et al. "Synthetic CT noise emulation in the raw data domain," in Nuclear Science Symposium Conference Record (NSS/MIC), 2010 IEEE, 2010, pp. 3169-3171.
R. M. S. Joemai et al., "Development and validation of a low dose simulator for computed tomography.," European Radiology, (2010) vol. 20, No. 4, pp. 958-966.
K. Tsiklakis et al."Dose reduction in maxillofacial imaging using low dose cone beam CT," European Journal of Radiology, vol. 56 (2005) No. 3, pp. 413-417.
P. Massoumzadeh et al., "Validation of CT dose-reduction simulation," Medical Physics, vol. 36, No. 1, Jan. 2009, p. 174.
S. Žabic et al., "A low dose simulation tool for CT systems with energy integrating detectors," Medical Physics, vol. 40 (3), Mar. 2013, p. 31102.
J. R. Mayo et al., "Simulated dose reduction in conventional chest CT: validation study.," Radiology, 1997, vol. 202, No. 2, pp. 453-457.
A. S. Wang et al., "Image-based synthetic CT: simulating arbitrary low dose single and dual energy protocols from dual energy images," in Proceedings of SPIE, 2012, vol. 8313, p. 83131G.
J. H. Siewerdsen et al., "Spektr: A computational tool for x-ray spectral analysis and imaging system optimization," Medical Physics, vol. 31, No. 11, Nov. 2004, pp. 3057-3067.
A. S. Wang et al., "Soft-tissue imaging with C-arm cone-beam CT using statistical reconstruction," Physics in Medicine and Biology, Feb. 21, 2014, vol. 59, No. 4, pp. 1005-1029.
A. S. Wang et al. "Synthetic CT: Simulating low dose single and dual energy protocols from a dual energy scan," Medical Physics, vol. 38, No. 10, Oct. 2011, pp. 5551-5562.
K. J. Strauss et al. "The ALARA (As Low As Reasonably Achievable) Concept in Pediatric Interventional and Fluoroscopic Imaging: Striving to Keep Radiation Doses as Low as Possible during Fluoroscopy of Pediatric Patients-A White Paper Executive Summary," Radiology, 2006, vol. 240, pp. 621-622.
D.P. Frush et al., "Computer-Simulated Radiation Dose Reduction for Abdominal Multidetector CT of Pediatric Patients", AJR, 179, Nov. 2002.
J. W. Stayman et al. "Task-based trajectories in iteratively reconstructed interventional cone-beam CT," The 12th International Meeting on Fully Three-Dimensional Image Reconstruction in Radiology and Nuclear Medicine, 2013, pp. 257-260.
R. C. Orth et al., "C-arm cone-beam CT: general principles and technical considerations for use in interventional radiology.," Journal of Vascular and Interventional Radiology: JVIR, 2008, vol. 19, No. 6, pp. 814-820.
J. H. Siewerdsen et al., "Signal, noise power spectrum, and detective quantum efficiency of indirect-detection flat-panel imagers for diagnostic radiology," Medical Physics, vol. 25, No. 5, May 1998 p. 614.
R. R. Galigekere et al. "Cone-beam reprojection using projection-matrices," Medical Imaging, IEEE Transactions on Medical Imaging, vol. 22, No. 10, Oct. 2003, pp. 1202-1214.
M. J. Daly et al., "Intraoperative cone-beam CT for guidance of head and neck surgery: Assessment of dose and image quality using a C-arm prototype," Medical Physics, vol. 33 (10) Oct. 2006, p. 3767.
S.-J. Tu et al., "Noise simulation in cone beam CT imaging with parallel computing.," Physics in Medicine and Biology, Mar. 7, 2006, vol. 51, No. 5, pp. 1283-1297.
M. J. Wallace et al., "Three dimensional C-arm cone-beam CT: applications in the interventional suite," Journal of Vascular and Interventional Radiology, 2008, vol. 19, pp. 799-813.
S. Schafer et al., "Mobile C-arm cone-beam CT for guidance of spine surgery: Image quality, radiation dose, and integration with interventional guidance," Medical Physics, vol. 38 (8), Aug. 2011, p. 4563.
L. Yu et al., "Development and validation of a practical lower-dose-simulation tool for optimizing computed tomography scan protocols.," Journal of Computer Aassisted Tomography, vol. 36, No. 4, Jul./Aug. 2012,pp. 477-487.
J. H. Siewerdsen et al., "Volume CT with a flat-panel detector on a mobile, isocentric C-arm: Pre-clinical investigation in guidance of minimally invasive surgery," Medical Physics, vol. 32, No. 1, Jan. 2005, p. 241.

(56) References Cited

OTHER PUBLICATIONS

G.-H. Chen et al., "Design and development of C-arm based cone-beam CT for image-guided interventions: initial results," in Proceedings of SPIE, 2006, vol. 6142, No. 1, pp. 614210-614212.
K. Hanai et al. "Computer-simulation technique for low dose computed tomographic screening.," Journal of Computer Assisted Tomography, vol. 30, No. 6, Nov./Dec. 2006, pp. 955-961.
C. Won Kim et al. "Realistic simulation of reduced-dose CT with noise modeling and sinogram synthesis using DICOM CT images," Medical Physics, vol. 41, No. 1, Jan. 2014, p. 011901.
Wouter J.H. Veldkamp et al., "A Technique for Simulating the Effect of Dose Reduction on Image Quality in Digital Chest Radiography", Journal of Digital Imaging, vol. 22, No. 2, Apr. 2009, pp. 114-125.
A. C. Miracle et al."Conebeam CT of the head and neck, part 2: clinical applications," American Journal of Neuroradiology, vol. 30, Aug. 2009, pp. 1285-1292.
Wang et al., "Low-Dose Preview for Patient-Specific, Task-Specific Technique Selection in Cone-Beam CT", Medical Physics, vol. 41, No. 7, 2014, p. 071915.
Wang et al., "Patient-specific minimum-dose imaging protocols for statistical image reconstruction in C-arm cone-beam CT using correlated noise injection" in SPIE Medical Imaging, 2014, p. 90331P.

\* cited by examiner

FIG 1

Low ←— Radiation Dose —→ High

METHOD AND DEVICE FOR GENERATING A LOW-DOSE X-RAY IMAGE PREVIEW, IMAGING SYSTEM AND COMPUTER PROGRAM PRODUCT

CROSS-REFERENCE RELATED APPLICATION

This application claims the benefit, under 35 U.S.C. § 119(e), of provisional patent application No. U.S. 62/022,548, filed Jul. 9, 2014; the prior application is herewith incorporated by reference in its entirety.

BACKGROUND OF THE INVENTION

Field of the Invention

The invention describes a method of generating a preview of a low-dose x-ray image; a device for generating a low-dose x-ray image preview; and an imaging system for generating a preview of at least one low-dose x-ray image.

Figure 1:
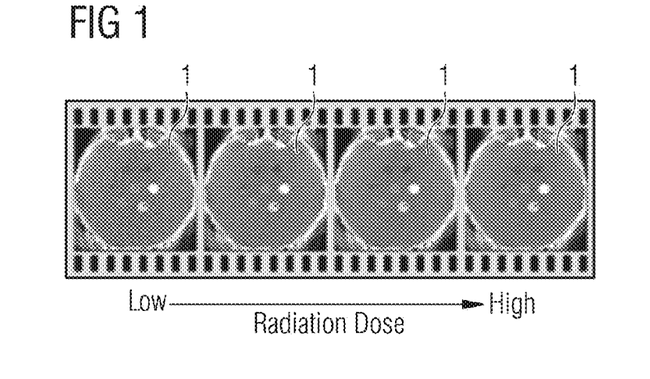
FIG. 1 shows a visual comparison of images as a function of x-ray dose.

Cone-beam computed tomography, or cone-beam CT (CBCT) is finding increased application in areas such as image-guided surgery (IGS), image-guided radiation therapy (IGRT), and interventional radiology. For example, in IGS, an initial CBCT may be used for patient setup and registration of preoperative planning information, while subsequent CBCTs may be used for visualizing surgical progress, detection of complications, and/or verifying the surgical product. In accordance with known efforts to reduce radiation dose to the patient (and in some cases to the clinicians, as with IGS), each CBCT should be acquired at the minimum dose such that a particular imaging task(s) can still be reliably performed. Of course, lower dose techniques generally produce higher noise images, as illustrated in FIG. 1, and the selection of the minimum-dose protocol for a particular patient is challenging, and is usually guided simply by a coarse technique chart in which scan protocols are simply stratified by patient body habitus. The ability to confidently select low-dose protocols sufficient for a given imaging task and a given patient is therefore a challenge, and perhaps even more so for nonlinear model-based image reconstruction (MBIR) methods for which complex dose-noise-resolution tradeoffs may defy a simple predictive model.

One method to aid in selecting a patient-specific and task-specific protocol (i.e., acquisition technique, image reconstruction method, and image processing/post-processing parameters) is to provide a "low-dose preview" (LDP) of the image quality that can be expected for a CBCT image acquired at reduced dose. Such simulated dose reduction methods have been developed and validated for diagnostic CT and used to establish low-dose CT protocols by allowing the user to visualize image quality at reduced dose, followed by confident selection of minimum-dose protocols sufficient for the imaging task. A known method demonstrated that by injecting noise into raw CT data to simulate dose reduction, the reconstructed CT images were indistinguishable from real low-dose images. Subsequent studies used simulated dose reduction to demonstrate the potential for low-dose protocols in applications such as pediatric abdominal CT, CT colonography, chest CT, and chest radiography. More recently, simulated dose reduction methods have utilized more advanced models of noise beyond just quantum noise, such as inclusion of electronic noise that led to accurate reproduction of not only image noise magnitude but also noise power spectra. Other extensions of simulated dose reduction include using dual energy scans to allow simulated changes in tube voltage or using an image-based approach that does not assume availability of projection data (but does not allow for different reconstruction methods/parameters). Common to these methods is the assumption of spatially uncorrelated noise in the projection data, which may be a fair assumption for detectors employed in multi-detector CT scanners. However, correlated noise is an important consideration for flat-panel detectors (FPDs) that are typically used in CBCT. For example, scintillator blur is known to introduce spatial correlation in the quantum noise, and electronic noise can be an important source of noise at very low dose levels. Correlated noise includes noise other than purely random noise. Therefore, previous methods for low-dose simulation in CT cannot be directly extended to CBCT based on indirect-detection FPDs since they do not include the effect of correlated noise (quantum or electronic noise).

To address these needs, a LDP method was previously developed for FPD-based CBCT that seeks to inject both quantum noise and electronics noise in a manner that is accurate in terms of both the magnitude and correlation of noise exhibited at a lower dose (A. S. Wang, J. W. Stayman, Y. Otake, S. Vogt, G. Kleinszig, A. J. Khanna, G. L. Gallia, and J. H. Siewerdsen, "Low-Dose Preview for Patient-Specific, Task-Specific Technique Selection in Cone-Beam CT," *Medical Physics*, vol. 41, no. 7, p. 071915, 2014; A. S. Wang, J. W. Stayman, Y. Otake, A. J. Khanna, G. L. Gallia, and J. H. Siewerdsen, "Patient-specific minimum-dose imaging protocols for statistical image reconstruction in C-arm cone-beam CT using correlated noise injection," in *SPIE Medical Imaging*, 2014, p. 90331 P). The LDP operates upon the initial CBCT of the patient (i.e., the first CBCT in a series of subsequent images, as in IGS or fractionated IGRT) to generate simulated low-dose projection data that are in turn reconstructed by whatever algorithm and post-processing methods are available in the imaging system, forming a CBCT-to-CBCT LDP, or $LDP_{CBCT}^{CBCT}$. In using the observer's own preferences to select the minimum-dose protocol for a particular imaging task, this approach to prospective protocol selection is independent of models of observer performance; moreover, by operating on the actual projection data from the initial CBCT scan, it is patient-specific and applicable to advanced image reconstruction and processing methods (including MBIR and possible proprietary artifact correction or post-processing methods incorporated by a particular system).

Tradeoff between radiation dose and CBCT image quality is easily appreciated when presented with a visual comparison of images as a function of dose, with increasing image noise at lower dose, as illustrated in FIG. 1. The minimum-dose protocol for a certain imaging task is dependent on the specific patient and reconstruction method used.

However, the developed $LDP_{CBCT}^{CBCT}$ method requires a previously acquired ("initial") CBCT to preview subsequent CBCTs and can only preview lower exposure techniques, with other aspects such as geometry, orbit, field of view, and/or tube voltage/filtration constrained to that of the initial CBCT.

SUMMARY OF THE INVENTION

It is accordingly an object of the invention to provide a method and a device for generating a low-dose x-ray image preview which overcome the above-mentioned and other disadvantages of the heretofore-known devices and methods of this general type and which provides for an improved method for previewing patient-specific images at low-dose protocols that allows prospective protocol selection to be performed in a better-informed manner.

With the foregoing and other objects in view there is provided, in accordance with the invention, a method of generating a preview of a low-dose x-ray image. The novel method comprising the following steps:

obtaining an initial volumetric representation of a patient by an x-ray device;

creating one or more x-ray image projections from the initial volumetric representation;

injecting correlated noise into at least one of the x-ray image projections to form one or more noise-injected x-ray image projections;

processing the noise-injected x-ray image projections to generate at least one preview of a patient-specific low-dose x-ray image for display to a user according to a task specific to the patient.

In other words, according to the invention, the method of generating a preview of at least one low-dose x-ray image comprises the steps of obtaining an initial volumetric representation of a patient by an x-ray device; creating at least one simulated x-ray image projection from the initial volumetric representation; injecting correlated noise into at least one of the simulated x-ray image projections in order to simulate "realistic" low-dose cone-beam projections; and processing the noise-injected x-ray image projections to create at least one preview of a "reconstructed" intraoperative patient-specific low-dose x-ray image for showing to a user.

An advantage of the method according to the invention is that it enables preview of low-dose images. With the low-dose previews, a user can assess image quality for scans at various dose levels, allowing prospective selection of an optimum x-ray dose specific to the patient and imaging task, for application in a subsequent image-guided intervention.

With the above and other objects in view there is also provided, in accordance with the invention, a device for generating at least one preview of a low-dose x-ray image. The device comprises:

a data processor and a display device in communication with said data processor, said data processor being configured to:

obtain an initial volumetric representation of a patient by way of an x-ray device;

create at least one x-ray image projection from the initial volumetric representation;

inject correlated noise into at least one of the x-ray image projections to form at least one noise-injected x-ray image projection;

process the at least one noise-injected x-ray image projection to generate at least one preview of a patient-specific low-dose x-ray image for display to a user on said display device.

In other words, according to the invention, there is provided a device for generating previews of a low-dose x-ray image with a data processor and a display device in communication with the data processor. The data processor is configured to: obtain an initial volumetric representation of a patient by an x-ray device; create at least one simulate x-ray image projection from the initial volumetric representation; inject correlated noise into at least one of the simulated x-ray image projections in order to simulate "realistic" low-dose cone-beam projections; and to process the noise-injected x-ray image projections to create at least one preview of a reconstructed intraoperative patient-specific low-dose x-ray image for showing to a user on the display device.

According to the invention, the imaging system for generating a preview of at least one low-dose x-ray image comprises the inventive device, and also an x-ray device—preferably a cone-beam computer tomograph—in communication with the data processor. The data processor of the device is configured to show the low-dose x-ray image previews on the display device to a user for selection of a protocol for an imaging task using the x-ray device.

An advantage of the device and imaging system according to the invention is that they allow a user such as a surgeon to visually compare preview images in order to choose a suitable radiation dose for the patient.

The dependent claims and the following description disclose particularly advantageous embodiments and features of the invention. Features of the embodiments may be combined as appropriate. Features described in the context of one claim category can apply equally to another claim category.

In the following, it may be assumed that a preview is an image obtained by processing the initial volumetric CT data to simulate a CBCT view of the patient during an image-guided intervention.

Preferably, the initial volumetric representation is a preoperative or diagnostic computed tomography scan, and the low-dose x-ray image preview simulates an intraoperative cone-beam computed tomography image. According to the invention, the correlated noise injected into an x-ray image projection preferably represents a reduced x-ray exposure dose. The previews effectively allow the user to assess—in advance of an image-guided intervention—the image quality that can be achieved at each of various x-ray dose levels.

To provide informative previews to the user, aspects specific to CBCT—such as geometry, orbit, field of view, and/or tube voltage/filtration—should be considered. Therefore, in a particularly preferred embodiment of the invention, the step of creating an x-ray image projection based on the initial volumetric representation comprises a step of simulating tube voltage and filtration, and/or beam hardening, and/or detector energy response of a cone-beam computer tomograph. In a further preferred embodiment of the invention, the step of creating the x-ray image projection can include a step of adding scatter. Additionally, in a further preferred embodiment of the invention, the step of creating an x-ray image projection can include a step of introducing system blur.

Tools or devices, typically composed of metal, may be used during image-guided intervention, and can have a drastic effect on image quality. Therefore, in a particularly preferred embodiment of the invention, the step of creating an x-ray image projection based on the initial volumetric representation comprises a step of virtually inserting an additional object into the x-ray image projection. The additional object can preferably comprise a surgical tool, an implantable device, an interventional device, a metallic object, etc.

In certain intervention procedures, material is removed from a patient. For example, an existing device or implant (for example one or more titanium screws) may be removed; or an existing tumor or lesion may be excised. Therefore, in a particularly preferred embodiment of the invention, the step of creating a CBCT x-ray image projection based on the initial volumetric CT representation comprises a step of virtually removing an object from the x-ray image projection to simulate the virtual removal of material from the patient.

In the method for generating a preview of a low-dose x-ray image according to the invention, the preview of at least one low-dose x-ray image represents at least one of a variation of detector blur and a variation of detector gain. The reconstructed x-ray image can be at least one of a radiographic image, a fluoroscopic image, a tomosynthesis reconstruction, a computed tomography reconstruction, and a cone-beam computed tomography reconstruction. An x-ray imaging device includes at least an emitter and a detector. The at least one x-ray image projection simulates at least one of a virtual addition of material into the patient, and/or a virtual removal of material from the patient.

According to the invention, a device for generating a preview of at least one low-dose x-ray image comprises at least one storage unit in communication with an x-ray device for obtaining an initial volumetric representation of a patient from the x-ray device; at least one data processor in communication with the at least one storage unit and an x-ray device; and at least one display device in communication with the at least one storage unit and the at least one data processor; wherein the at least one processor is configured to obtain the initial volumetric representation of a patient from the x-ray device; to create at least one x-ray image projection of the patient based on the initial volumetric representation; to inject correlated noise into the at least one x-ray image projection; to reconstruct the at least one x-ray image projection according to a task specific to the patient; and to display, at the at least one display device, a preview of the at least one low-dose x-ray image based on the reconstruction of the at least one x-ray image projection. Preferably, the device can enable a selection of a preview, i.e. it can allow a user to select a suitable preview from several previews displayed on the display device.

Preferably, the initial volumetric representation of the patient is a prior diagnostic image, most preferably a computed tomography volume obtained directly or indirectly from a computer tomograph. In the device according to the invention, the correlated noise injected into the at least one x-ray image projection represents reduced x-ray exposure. Furthermore, the preview of the at least one low-dose x-ray image projection preferably represents at least one of a variation of detector blur and a variation of detector gain.

In a further preferred embodiment of the device according to the invention, the at least one reconstructed x-ray image is at least one of a radiographic image, a fluoroscopic image, a tomosynthesis reconstruction, a computed tomography reconstruction, and a cone-beam computed tomography reconstruction. Preferably, the reconstructing of the at least one x-ray image includes at least one of a filtered back-projection and a model-based image reconstruction. In the device according to the invention, the at least one x-ray image projection preferably simulates at least one of a virtual addition of material into the patient and a virtual removal of material from the patient. Furthermore, in the device according to the invention, the virtually added material is at least one of a surgical tool, an implantable device, an interventional device, a metallic object; whereas the virtually removed material can be a tumor, a lesion, etc.

The non-transitory computer readable medium according to the invention preferably comprises software, which software when executed by a computer causes said computer to obtain, by at least one processor, an initial volumetric representation of a patient by an x-ray device; to create, by the at least one processor, at least one x-ray image projection of the patient based on the initial volumetric representation; to inject, by said at least one processor, correlated noise into said at least one x-ray image projection; to reconstruct, by said at least one processor, said at least one x-ray image projection according to an algorithm specific to a task of said patient and based on said injecting of said correlated noise; and to display a preview of said at least one low-dose x-ray image based on said reconstruction of said at least one x-ray image projection; Preferably, the software allows a user to make a selection of a preview. Preferably, the initial volumetric representation of said patient is a prior diagnostic image, most preferably a computed tomography volume. The correlated noise injected into the at least one x-ray image projection preferably represents reduced x-ray exposure. The preview of said at least one low-dose x-ray image preferably represents at least one of a variation of detector blur and a variation of detector gain. Preferably, the reconstructed x-ray image projection is at least one of a radiographic image, a fluoroscopic image, a tomosynthesis reconstruction, a computed tomography reconstruction, and a cone-beam computed tomography reconstruction. The reconstructing of an x-ray image projection preferably includes at least one of a cone-beam filtered back-projection and a model-based image reconstruction. Preferably, an x-ray image projection simulates at least one of a virtual addition of material into said patient and a virtual removal of material from said patient.

Other features which are considered as characteristic for the invention are set forth in the appended claims.

Although the invention is illustrated and described herein as embodied in a method and device of generating a low-dose x-ray image preview, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE SEVERAL VIEWS OF THE DRAWING

In the drawing figures, identical and functionally corresponding objects are identified with like reference numbers throughout. Objects in the diagrams are not necessarily drawn to scale.

DETAILED DESCRIPTION OF THE INVENTION

Figure 2:
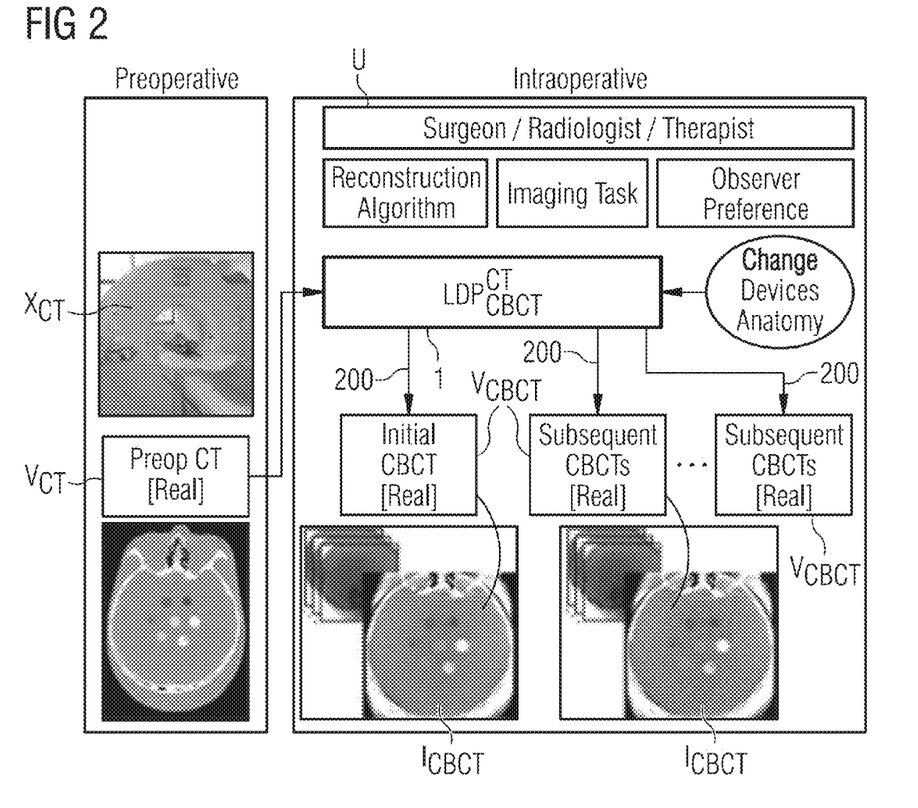
FIG. 2 is a block diagram illustrating a CT as source of volumetric data for the imaging system according to the invention.

The method according to the invention generalizes the CBCT image preview concept to any low-dose CBCT geometry, orbit, and/or technique (viz., tube voltage/filtration and exposure). Importantly, the inventive CT-to-CBCT LDP ($LDP_{CBCT}^{CT}$) method operates without requiring an initial CBCT. In many situations where CBCT is used, the patient has previously received diagnostic CT scan(s) (e.g., for preoperative planning purposes prior to IGS, or for treatment planning prior to IGRT). The new $LDP_{CBCT}^{CT}$ method provides a preview of any CBCT scan by utilizing a prior CT volume of the patient to simulate CBCT projections for arbitrary acquisition geometry and orbit, tube voltage (kVp) and filtration, and exposure (mAs), as shown in FIG. 2. The transformation from a CT volume VCT to simulated CBCT projections is central to $LDP_{CBCT}^{CT}$, and the correlated noise injection previously developed for $LDP_{CBCT}^{CBCT}$ still plays a critical role. A description of the methodology is provided below in an IGS context—however, the LDPs are similarly applicable to other CBCT contexts, including IGRT and image-guided interventions.

FIG. 2 shows a workflow for image-guided surgery. Imaging is provided by way of a preoperative CT volume VCT and intraoperative CBCT volumes VCBCT ("real" scans). Within the operating room, an expert CBCT user U such as a surgeon can provide a wealth of knowledge to determine the minimum-dose CBCT protocol 200, including knowledge of the desired reconstruction method and post-processing parameters, the imaging task at hand, and the user's own observer preferences. The $LDP_{CBCT}^{CT}$ method according to the invention augments this knowledge and thereby allows an informed selection of the minimum-dose protocol, whether by previewing a first CBCT prior to the planned intervention, or any subsequent CBCTs during the intervention. Change in the CBCT such as the insertion of interventional devices can also be previewed virtually, as will be explained below.

The starting point for $LDP_{CBCT}^{CT}$ is a volumetric representation VCT of the patient, e.g., preoperative CT. Therefore, in order to ultimately simulate realistic low-dose cone-beam projections, the CT volume VCT must be re-projected while accounting for the entire physical forward model that produces x-ray projections. A high-level overview is given in FIG. 3.

Figure 3:
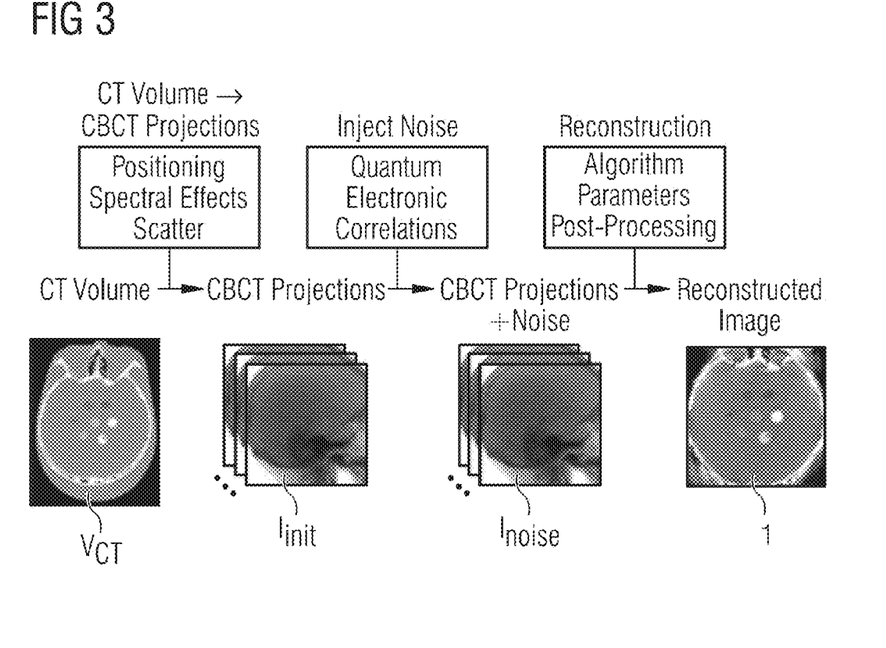
FIG. 3 is a schematic representation of stages in the method according to the invention.

FIG. 3 shows a high-level overview of the inventive $LDP_{CBCT}^{CT}$ method, which generates realistic CBCT projections from a CT volume VCT by simulating the entire physical forward model to obtain a reconstructed $LDP_{CBCT}^{CT}$ image 1. A more detailed overview of the steps specific to the inventive $LDP_{CBCT}^{CT}$ method is as follows:

| CT Volume ↓ CBCT Projections | 1. CT Volume | Use high-quality CT volume |
|---|---|---|
| | 2. Positioning | Manually set C-arm FOV |
| | 3. Forward Project | Segment water/bone and re-project |
| | 4. Spectral Effects | Source spectrum Beam hardening Detector energy response |
| | 5. Scatter | Constant per projection |
| | 6. System Blur | Source/detector blur |
| | 7. Noise | Inject correlated noise |
| | 8. Reconstruction | Compatible with any method Can preview reconstruction parameters |

The steps are illustrated graphically in FIG. 3, and described in the following:

CT Volume: The $LDP_{CBCT}^{CT}$ leverages a volumetric representation $V_{CT}$ of the patient (such as a preoperative CT) to simulate realistic CBCT projections. Desirable properties of the CT volume $V_{CT}$ include an untruncated reconstruction, high-resolution reconstruction (voxel size and reconstruction kernel), and low-noise images. For a CT volume $u_{CT}$ (in Hounsfield units HU), the volume is first segmented into material classes. For example, normal human anatomy may be separated as mass density of water and bone: $\rho_{water}$, $\rho_{bone}$ by thresholding the CT volume at value T (e.g., 400 HU):

$$\rho_{water} = \begin{cases} 1 + \frac{u_{CT}}{1000}, & u_{CT} \leq T \\ 0, & u_{CT} > T \end{cases} \quad (1)$$

$$\rho_{bone} = \begin{cases} 0, & u_{CT} \leq T \\ 1 + \frac{u_{CT}}{1000}, & u_{CT} > T \end{cases}$$

In practice, the above can be modified to incorporate a soft threshold that transitions the segmentation from water to bone over a range of HU values (e.g., 300 to 500 HU). Moreover, additional material classes can also be considered (for example, $\rho_{titanium}$ for a titanium surgical device) and superimposed onto the CT volume.

B. Positioning: A user-specified CBCT field of view (FOV), acquisition geometry, and/or acquisition orbit can be previewed to better inform the user how such selections affect image quality and the ability to accomplish the desired imaging task(s). The user U can either manually input these selections, or they could be custom-designed (e.g. using a known optimized task-based trajectory) to the extent that the CBCT system is capable.

Alternatively, the CBCT FOV could be set to match that of an intraoperative setup. For example, 3D-2D registration offers the ability to determine the CBCT pose from a single projection (e.g., the first) with the patient and system set up in imaging position, which provides the FOV and geometry (e.g., as defined by projection matrices) relative to the solved pose of the single projection as will be known to the skilled person.

C. Forward Project: The set of all projections can be characterized by system matrix A, which defines the projections with respect to the CT volume. Material classes are forward-projected separately to determine the line integrals of each material mass density. For example, for water, the line integrals are:

$$l_{water} = A\rho_{water}. \quad (2)$$

D. Spectral Effects: Spectral properties of CBCT are included by simulating several effects:
polychromatic source spectrum $\Phi_0$ (E) that reflects the simulated CBCT tube voltage (kVp) and filtration;
beam hardening using the mass attenuation ($\mu/\rho$) (E) of each material; and
detector energy response D (E), i.e. the average signal produced for a photon of energy E, that reflects the CBCT detector energy response.

Using Beer's Law, the detected primary signal (for an object segmented into water and bone) is proportional to:

$$\Phi = \int D(E) \cdot \Phi_0(E) \exp\left\{-\left[l_{water} \cdot \left(\frac{\mu}{\rho}\right)_{water}(E) + l_{bone} \cdot \left(\frac{\mu}{\rho}\right)_{bone}(E)\right]\right\} dE. \quad (3)$$

E. Scatter: Scatter is accounted for by adding a scatter map S to each normalized projection, where $I_0$ is the flood-field (air scan) projection of the CBCT system. The scatter map can be determined by a number of methods, ranging from complex Monte Carlo simulations to basic analytic approximations.

$$A. \quad I = \frac{I_0 \cdot \Phi}{\int D(E) \cdot \Phi_0(E) dE} + S \quad (4)$$

F. System Blur: CBCT systems typically experience system blur from a finite source size and/or detector blur such as that experienced with indirect-conversion scintillators. The CBCT system-specific blur can be characterized by a point-spread function p. However, p may be modified to account for spatial resolution loss already present in the CT volume (which is dependent on the CT system, acquisition, and reconstruction) and the re-projection process (e.g., forward-projection model). The projections can then be modified by 2D convolution with p as follows:

$$I_{init} = I*p, \quad (5)$$

assuming a spatially-invariant blur.

G. Noise: The resulting projections $I_{init}$ (indicated as a stack of x-ray images in the diagram) are the simulated CBCT projections originating from the CT volume $V_{CT}$. Correlated noise accounting for both quantum and electronic noise magnitude and correlations can then be injected, as in the case of $LDP_{CBCT}^{CBCT}$, to give noise-injected projections $I_{noise}$. Note, however, that the initial noise cannot be determined in the same manner as in $LDP_{CBCT}^{CBCT}$ due its complex dependence on the re-projection of the CT volume, which itself has noise properties that depend on the CT system, scan technique, and reconstruction method. Preferably, therefore, a nominal equivalent CBCT technique is assumed, from which the initial noise level can be set. The LDP and injected noise levels are still derived in the same manner as $LDP_{CBCT}^{CBCT}$.

H. Reconstruction: Lastly, the realistic simulated CBCT previews 1 can be reconstructed using any desired method (e.g., filtered back-projection, or model-based iterative reconstruction), with any set of artifact correction methods, reconstruction parameters, and post-processing methods. These reconstructed images 1 are then presented to the user U as the $LDP_{CBCT}^{CT}$ preview images 1.

Figure 4:
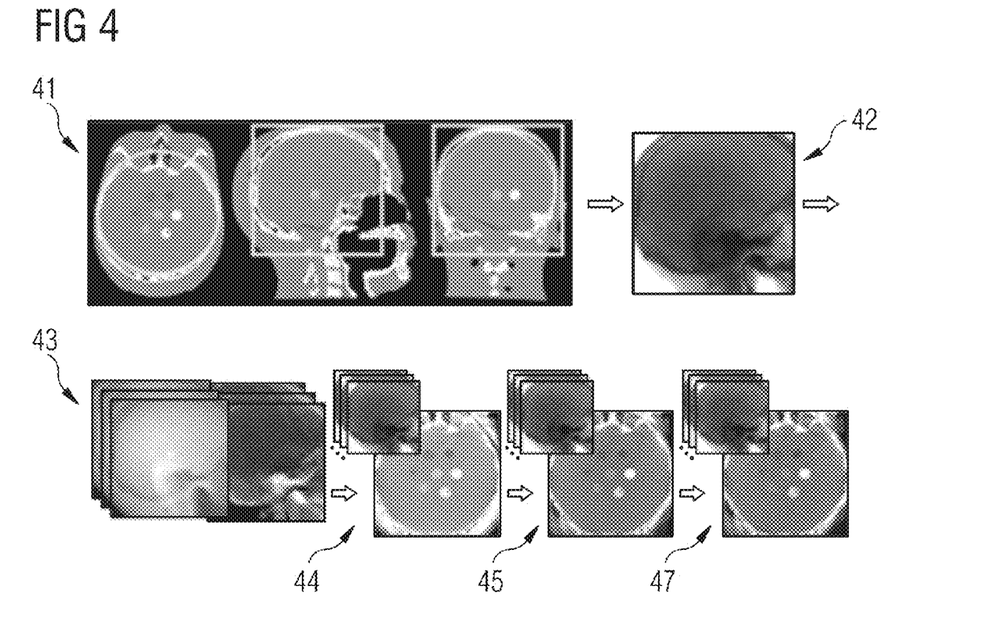
FIG. 4 is a further schematic representation of stages in the method according to the invention.

FIG. 4 illustrates stages 41-47 of the inventive method for transforming a CT volume $V_{CT}$ into simulated CBCT projections for creating $LDP_{CBCT}^{CT}$ preview images 1. Each stage 41-47 is indicated by an exemplary image indicating the level of progress. Starting with a high-quality CT volume $V_{CT}$ in stage 41, the CBCT field of view and imaging geometry is set with respect to the CT volume (as shown by the rectangular frame). This can be done manually by the user to preview a desired region, or automated by way of a single real CBCT projection and 3D-2D registration, arriving at stage 42. In stage 43, the CT volume is segmented into material classes such as water and bone, and the materials are re-projected separately. Spectral effects are included at stage 44 by applying Beer's Law to attenuate a polyenergetic source spectrum through the material classes and accounting for the detector's spectral response. Scatter is added to the projections in stage 45. CBCT system blur can be introduced at this point, while accounting for blur already present in the CT volume and incurred by the re-projection of the volume. In this example, no additional blur was introduced, effectively skipping step 6 described above. In stage 47, correlated noise is injected into the projections. Reconstructed image(s) 1, i.e. the $LDP_{CBCT}^{CT}$ previews obtained after performing the method steps, are shown to the user. The small stacks of reconstructed images shown for the simulated projections at stages 44, 45, 47 are for illustrative purposes only.

Experiments were conducted with a prototype mobile C-arm (modified Powermobil™, Siemens Healthcare) capable of CBCT acquisitions across a wide range of dose levels by varying the x-ray tube current (e.g., 20-320 mAs) at a fixed tube voltage (100 kVp), and comprising a processor for processing the CBCT data, and one or more display units for showing projections to the user. Real CBCT scans of an anthropomorphic head phantom (obtained from The Phantom Laboratory, Greenwich, N.Y.) and a cadaveric torso were compared with $LDP_{CBCT}^{CT}$ images. Although the simulated LDP projections can be reconstructed with any method and set of parameters, for simplicity, only one reconstruction method (which is representative of various MBIR algorithms) is shown here, i.e. penalized likelihood (PL) with an edge-preserving Huber penalty, and parameters: $\delta=10^{-3}$ mm$^{-1}$ and $\beta$ numerically equivalent to the scan current (e.g., $\beta=20$ for the 20 mAs scan), as will be familiar to the skilled person. The reconstruction method was applied consistently to the simulated $LDP_{CBCT}^{CT}$ projections and the real CBCT scans so that any differences in image quality were due to differences in the projections.

Details particular to these experiments and relating to the steps of the inventive method of generating $LDP_{CBCT}^{CT}$ images are as follows:

CT Volume: CT scans (SOMATOM Definition Flash, Siemens Healthcare) were acquired at 120 kVp, 400 mAs and reconstructed with the H60s kernel and 0.5× 0.5×0.5 mm$^3$ voxels for the head phantom, and acquired at 120 kVp, 500 mAs and reconstructed with the H70h kernel and 0.67×0.67×0.6 mm$^3$ voxels for the cadaveric torso.

Positioning: 3D-2D registration was used to match the simulated CBCT FOV with the setup of the real CBCT scans for a consistent comparison, and the previously acquired geometric calibration of the system was used to provide the same projection matrices as the C-arm acquisition, as will be known to the skilled person.

Forward Project: Water and bone were segmented in the CT volume using a soft threshold between 300 to 500 HU. A separable footprints (SF-TT) projector was used due to its higher levels of accuracy, as will be familiar to the skilled person.

Spectral Effects: A computational tool "Spektr", with which those of skill in the pertinent are will be familiar, was used to simulate a 100 kVp spectrum with 2.5 mm Al filtration, compute the mass attenuation of water and bone, and determine the detector energy response for a 550 μm thick CsI scintillator.

Scatter: A constant value was added per projection, which was set as a fraction (e.g., 60%) of the first percentile value of the projection (pre-scatter).

System Blur: No additional system blur was introduced, so this step was effectively skipped.

Noise: Initial noise from the CT volume was assumed to be zero, and the LDP noise was set by the simulated technique (e.g., 20 mAs).

Figure 5A:
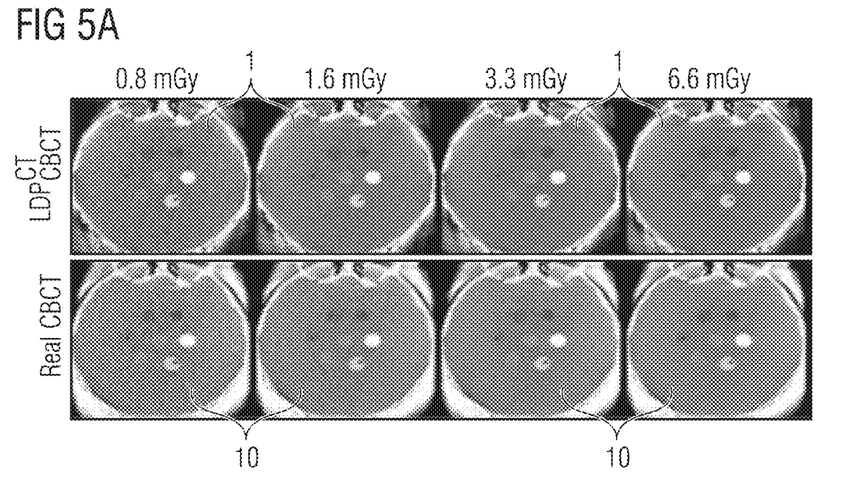
FIG. 5A shows preview CBCT images and real CBCT images at four dose levels.

FIGS. 5A-5E illustrate the LDP validation study using an anthropomorphic head phantom. FIG. 5A shows $LDP_{CBCT}^{CT}$ preview images 1 and real CBCT images 10 at four dose levels. $LDP_{CBCT}^{CT}$ images 1 for the anthropomorphic head phantom are shown at various dose levels in the upper row of FIG. 5A. The real CBCT images 10 acquired at the specified dose levels are shown in the bottom row of FIG. 5A. The increase in image noise and resulting degradation of image quality at lower dose is captured well by the LDP. Even beam hardening artifacts are depicted since a full spectral model was included. On the other hand, some differences can be seen, such as the enhancement just outside the C-arm FOV that is not present in the $LDP_{CBCT}^{CT}$ images, possibly due to the simple scatter model used or other secondary effects not modeled. Nonetheless, the $LDP_{CBCT}^{CT}$ is representative of overall CBCT image quality and can be used to arrive at a well-informed protocol selection.

Figure 5B:
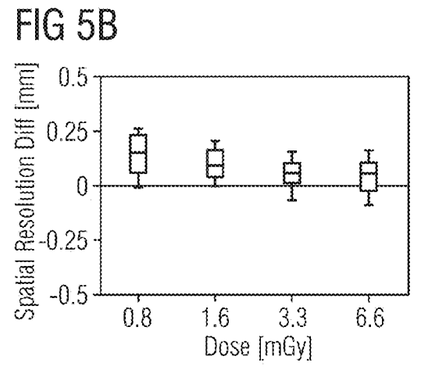
FIG. 5B shows a difference in measured spatial resolution between the images of FIG. 5A.
Figure 5C:
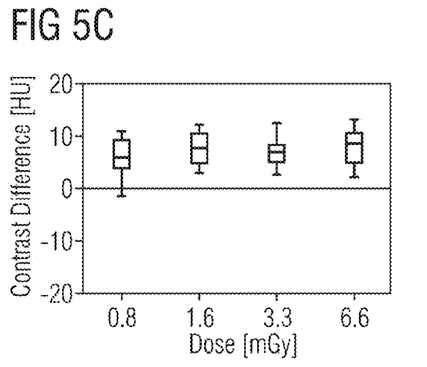
FIG. 5C shows a comparison of contrast between the images of FIG. 5A.
Figure 5D:
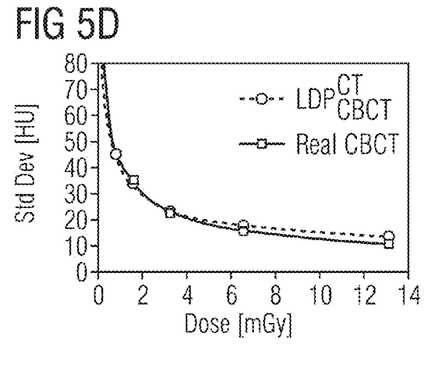
FIG. 5D shows image noise as a function of dose for the images of FIG. 5A.

A quantitative comparison between the LDP preview images 1 and real CBCT images 10 is presented in FIGS. 5B-5D. FIG. 5B shows the difference in measured spatial resolution between $LDP_{CBCT}^{CT}$ preview images 1 and real CBCT images 10. First, spatial resolution was quantified by fitting an error function to the edge of the high-contrast sphere (at the "3 o'clock position" in each of the eight images 1, 10 in FIG. 5A). The derivative of the error function provided a Gaussian whose full-width at half maximum (FWHM) was used as a metric of spatial resolution and compared between the LDP images 1 and real images 10. The difference in spatial resolution is plotted in FIG. 5B, showing that the $LDP_{CBCT}^{CT}$ did exhibit a slightly increased edge spread FWHM (on average ~100 μm greater). This was largely due to the re-projection of the reconstructed CT volume, a process that generally produces lower spatial resolution than the original CT projections. Nonetheless, the increase in edge spread FWHM is relatively minor compared to the voxel size (0.6×0.6×0.6 mm³) and edge spread FWHM ~0.8 mm.

The contrast of the seven spheres embedded in the phantom was compared in FIG. 5C. A small bias was observed, with the $LDP_{CBCT}^{CT}$ preview images 1 having ~8 HU higher contrast than the real CBCT images 10. Potential sources of this error could arise from an imperfect spectral model or not enough scatter being added. Nonetheless, this small bias in contrast is relatively minor compared to the absolute contrast levels of the spheres, which range from ~40 to 900 HU.

Image noise was measured by taking the standard deviation of a uniform region of the phantom. The $LDP_{CBCT}^{CT}$ image noise was in fairly strong agreement with the real CBCT images 10, though showing higher noise at higher dose (FIG. 5C). Due to the challenges associated with estimating the noise present in the CT volume and propagating that to an estimate of the initial noise in the simulated CBCT projections, this aspect was not considered. Therefore, at higher simulated dose levels, the noise originating from the CT volume was unaccounted for and contributed to the overall noise level. Determining the CT noise by way of an equivalent initial CBCT technique can perhaps be done by empirical studies that map CT techniques to equivalent CBCT techniques.

Figure 5E:
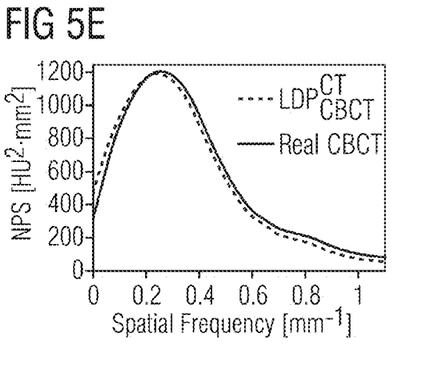
FIG. 5E shows a radially-averaged axial noise power spectrum for the images of FIG. 5A.

Finally, image noise as a function of dose is illustrated in FIGS. 5D, 5E: the noise power spectrum (NPS) is compared for the images 1, 10 at 1.6 mGy in FIG. 5D. The strong agreement in the radially-averaged axial NPS, shown in FIG. 5E, indicates that in addition to realistic image noise magnitude, the LDP methods produce realistic noise texture. This is a key feature of LDPs since the NPS is known to play an important role in detectability and performing imaging tasks.

Figure 6A:
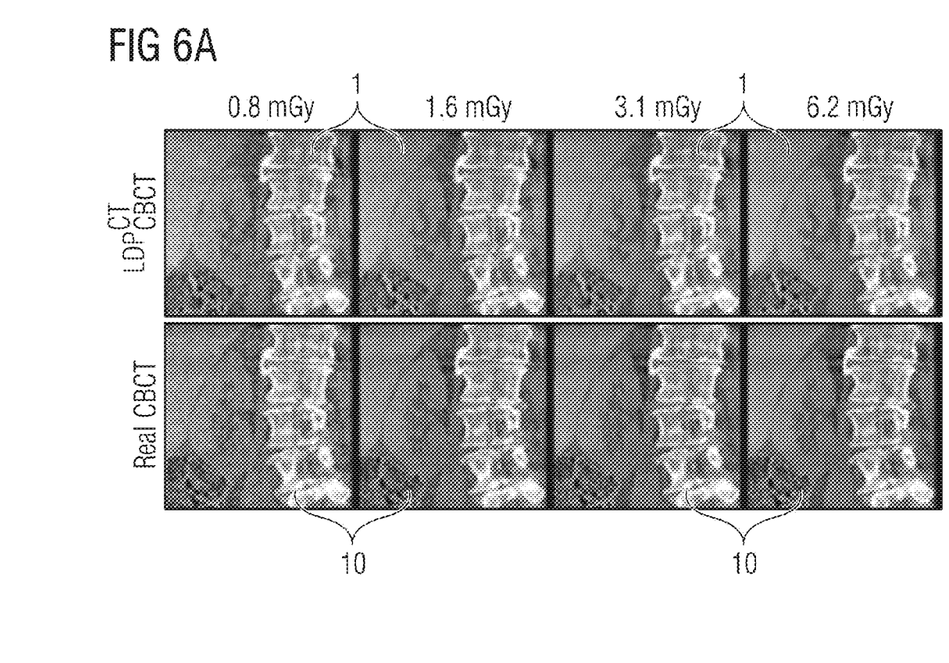
FIG. 6A shows preview CBCT images and real CBCT images at four dose levels.
Figure 6B:
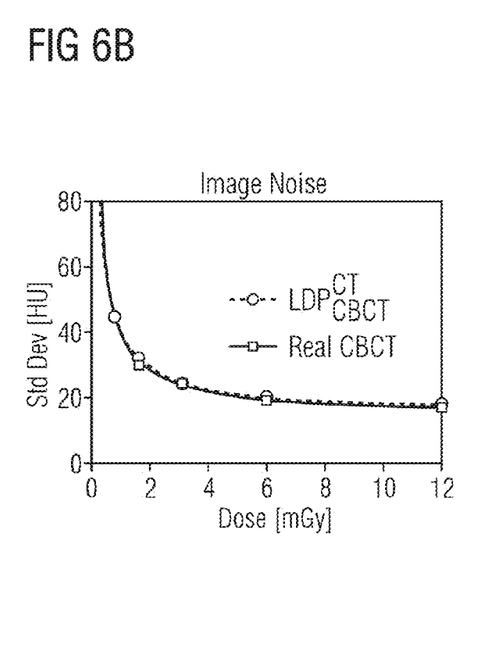
FIG. 6B shows image noise as a function of dose for the images of FIG. 6A.

The inventive $LDP_{CBCT}^{CT}$ method was similarly verified in a cadaveric torso where it offered realistic image quality by demonstrating the increased noise at lower dose and providing visualization of soft-tissue contrast of the kidney, liver, muscle, and fat; high-contrast, fine-detail structures; and image artifacts such as beam hardening and cone-beam artifacts. FIG. 6A shows coronal slices of a volumetric reconstruction of a cadaveric torso (top row) as $LDP_{CBCT}^{CT}$ preview images 1 as a function of dose (increasing to the right). The bottom row shows real CBCT images 10 acquired at the specified dose levels. Note that deformations introduced between the CT and CBCT scans of the cadaver can be seen in some structures (e.g., kidney), as would be expected in realistic scenarios, where a preoperative CT and intraoperative CBCT are acquired in different settings and often separated temporally by hours or days. Image noise was measured in a uniform region of the liver and showed strong agreement with the real CBCT images 10 at all acquired dose levels, suggesting that the initial CT noise was less of a factor in this case, as shown in FIG. 6B.

Figure 7A:
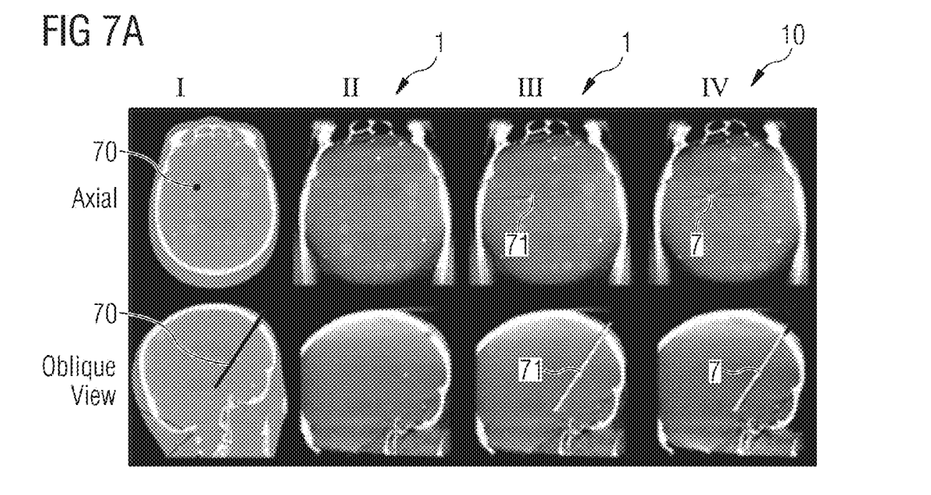
FIG. 7A shows preview CBCT images and real CBCT images illustrating a first interventional device.
Figure 7B:
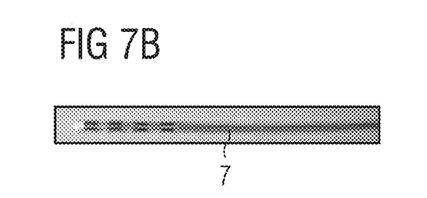
FIG. 7B shows a photograph of the interventional device imaged in FIG. 7A.
Figure 7C:
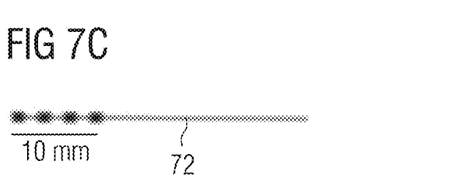
FIG. 7C shows a digital model of the interventional device imaged in FIG. 7A.

Lastly, the same process for simulating CBCT projections from CT volumes was extended to simulate the effect of additional objects captured by CBCT projections. This is particularly of interest for interventional/surgical tools or devices, which are typically composed of metal and can have a drastic effect on image quality. Therefore, by including them in the LDP, their effect can be visualized and accounted for during protocol selection. Given an object of known shape, composition, and position relative to the CBCT reference frame, the attenuation from the object can be incorporated in the projection, along with the patient anatomy. Examples are shown in FIG. 7, where a platinum deep brain stimulation (DBS) electrode was virtually placed inside the preoperative CT volume (which did not include the device) of an anthropomorphic head phantom. FIG. 7A shows $LDP_{CBCT}^{CT}$ images that include a virtual interventional device, in this case a DBS electrode. Axial views (top row) and oblique views (bottom row) are presented. Column I shows a preoperative CT volume with DBS electrode planning data 70 overlaid (indicated by the heavy line). Column II contains $LDP_{CBCT}^{CT}$ images 1 showing CBCT image quality prior to device insertion. Column III contains $LDP_{CBCT}^{CT}$ images 1 with the "electrode" 71 virtually inserted into the same location as the planning data. Column IV shows real CBCT images 10 with the electrode 7 inserted into the phantom. The diagram shows that the effect of the device 7 on CBCT image quality (e.g., metal artifacts) can be previewed before the actual intervention, and the optimal CBCT acquisition can be adjusted in advance according to the imaging task. FIG. 7B shows a photograph of the electrode 7. FIG. 7C shows a digital model of the electrode 72 based on its device specification sheet, e.g., 1.5 mm electrodes spaced 1.5 mm apart.

Figure 8A:
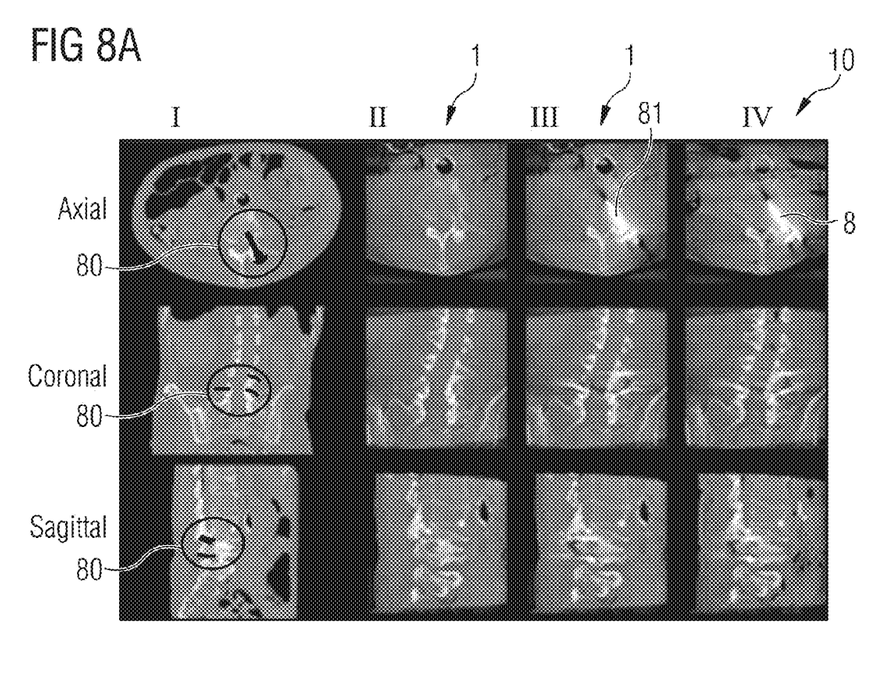
FIG. 8A shows preview CBCT images and real CBCT images illustrating a second interventional device.
Figure 8B:
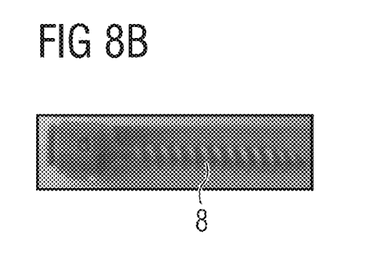
FIG. 8B shows a photograph of the interventional device imaged in FIG. 8A.
Figure 8C:
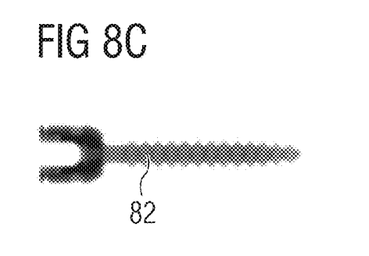
FIG. 8C shows a digital model of the interventional device imaged in FIG. 8A.

FIG. 8A shows $LDP_{CBCT}^{CT}$ images that include virtual surgical devices, in this case titanium pedicle spine screws 8. Axial views (top row), coronal views (middle row) and sagittal views (bottom row) are presented for a preoperative CT volume of a cadaveric torso, with planning data 50 for the titanium pedicle spine screws 8 overlaid as indicated in the encircled regions (Column I); $LDP_{CBCT}^{CT}$ preview images 1 showing CBCT image quality prior to screw 8 placement (Column II); $LDP_{CBCT}^{CT}$ preview images 1 with the "screws" 81 virtually inserted into the same location as the planning data (Column III); and real CBCT images 10 with screws 8 inserted (Column IV). Here also, the effect of the screws 8 on image quality (e.g. metal artifacts) can be previewed, and the optimal CBCT acquisition can be adjusted according to the imaging task. The LDP images (generated using conventional filtered back projection (FBP) reconstruction) clearly illustrate the effect of such devices on image quality that are typically associated with metal artifacts, including beam hardening, photon starvation, and blooming, but whose impact on image quality cannot be easily predicted without such visual aids. In both examples, a high-fidelity digital model of the device and its composition was available. FIG. 8B shows a photograph of the screw 8. Various methods exist for creating digital models, including CAD models provided by the manufacturer, device specification sheets, or by a high-quality scan of the device. FIG. 8C shows a manufacturer-supplied CAD model of the screw 5. High-fidelity projections (finely sampled voxels and detector pixels) were used to provide realistic nonlinear partial volume (NLPV) effects. The position of the devices in the LDP can either be set manually by the user or imported from preoperative planning data.

Figure 9:
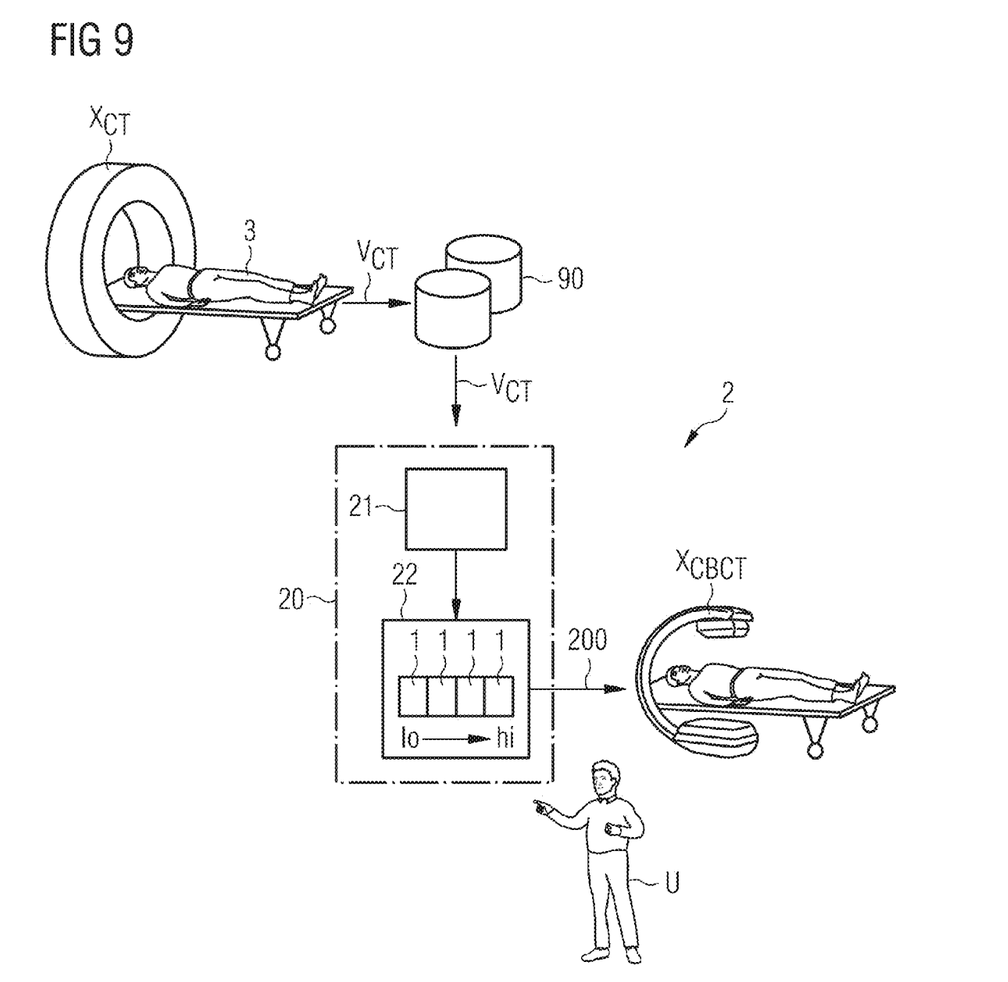
FIG. 9 is a schematic representation of an embodiment of an imaging system according to the invention.

FIG. 9 shows an embodiment of the imaging system 2 according to the invention. A device 20 comprises a data processor 21 which can load an initial CT volume $V_{CT}$ of a patient 3. The initial CT volume $V_{CT}$ can have been generated by a computer tomograph $X_{CT}$ as part of a pre-operative diagnostic procedure and may have been stored on a suitable storage medium 90 such as a hard-disk, USB stick, CD, etc. The initial CT volume $V_{CT}$ for the patient is input to the imaging system 2, and a processor 21 perform the processing steps of the inventive method initial CT volume $V_{CT}$ to compute low-dose previews at various levels of reduced x-ray exposure or dose. The imaging system 2 also comprises a display unit 21 to show a user U how inter-operative CBCT images will appear at various dose levels. Each low-dose preview 1 or LDP 1 is associated with a specific dose, and therefore also a certain CBCT protocol. The user U, for example a surgeon U, can choose the most suitable preview 1 and therefore its associated protocol 200 for the x-ray device $X_{CBCT}$ that will be used during the scheduled intervention, for example image-guided surgery.

A new method for previewing CBCT images from a CT volume has been presented and validated. This powerful new method enables the entire CBCT protocol to be freely selected and previewed, including acquisition parameters such as system geometry, acquisition orbit, and technique (kVp, filtration, mAs), reconstruction method/parameters, and post-processing algorithms. With $LDP_{CBCT}^{CT}$, users can now prospectively assess CBCT image quality for all scans, opening the possibility of fully-optimized protocols for each patient and imaging task. Extensions of $LDP_{CBCT}^{CT}$ that demonstrate the impact of interventional devices on image quality further enable the user to select optimal protocols in challenging imaging scenarios.

Although the present invention has been disclosed in the form of preferred embodiments and variations thereon, it will be understood that numerous additional modifications and variations could be made thereto without departing from the scope of the invention. For example, other embodiments may address the remaining differences in the $LDP_{CBCT}^{CT}$ spatial resolution, contrast, and noise by improving the physical forward model, including characterization of CT volume spatial resolution and noise, measurement of the CBCT system source spectrum and detector response, and incorporation of more accurate scatter models, etc.

For the sake of clarity, it is to be understood that the use of "a" or "an" throughout this application does not exclude a plurality, and "comprising" does not exclude other steps or elements.

The invention claimed is:

1. A method of generating a preview of a low-dose x-ray image, the method comprising the following steps:
   obtaining an initial volumetric representation of a patient by an x-ray device;
   creating one or more x-ray image projections from the initial volumetric representation;
   injecting correlated noise into at least one of the x-ray image projections to form one or more noise-injected x-ray image projections;
   processing the noise-injected x-ray image projections to generate at least one preview of a patient-specific low-dose x-ray image for display to a user according to a task specific to the patient.

2. The method according to claim 1, wherein the initial volumetric representation is a preoperative computed tomography scan.

3. The method according to claim 1, which comprises causing a low-dose x-ray image preview to simulate an intraoperative cone-beam computed tomography image.

4. The method according to claim 1, wherein the step of creating at least one x-ray image projection based on the initial volumetric representation comprises one of more of the following: simulating tube voltage and filtration, beam hardening, detector energy response of a cone-beam computer tomograph.

5. The method according to claim 1, wherein the step of creating an x-ray image projection based on the initial volumetric representation comprises adding scatter to the x-ray image projection.

6. The method according to claim 1, wherein the step of creating an x-ray image projection based on the initial volumetric representation comprises introducing system blur into the x-ray image projection.

7. The method according to claim 1, wherein the step of creating an x-ray image projection based on the initial volumetric representation comprises virtually inserting an additional object into the x-ray image projection.

8. The method according to claim 1, wherein the step of creating an x-ray image projection based on the initial volumetric representation comprises virtually removing material from the x-ray image projection.

9. The method according to claim 1, wherein the correlated noise injected into an x-ray image projection represents a reduced x-ray exposure.

10. The method according to claim 1, which comprises presenting previews at various, differing dose levels to a user for selection of a protocol for an imaging task.

11. The method according to claim 10, wherein the protocol comprises a cone-beam computer tomograph protocol including system geometry, orbit, and technique acquisition parameters; reconstruction parameters; and post-processing algorithms.

12. A device for generating at least one preview of a low-dose x-ray image, the device comprising:
a data processor and a display device in communication with said data processor, said data processor being configured to:
obtain an initial volumetric representation of a patient by way of an x-ray device;
create at least one x-ray image projection from the initial volumetric representation;
inject correlated noise into at least one of the x-ray image projections to form at least one noise-injected x-ray image projection;
process the at least one noise-injected x-ray image projection to generate at least one preview of a patient-specific low-dose x-ray image for display to a user on said display device.

13. An imaging system for generating a preview of at least one low-dose x-ray image, the imaging system comprising:
a data processor;
a display device in communication with said data processor; and
an x-ray device in communication with the data processor;
wherein said data processor is configured to:
obtain an initial volumetric representation of a patient;
create at least one x-ray image projection from the initial volumetric representation;
inject correlated noise into at least one of the x-ray image projections;
process the noise-injected x-ray image projections to create at least one preview of a patient-specific low-dose x-ray image;
show the at least one low-dose x-ray image preview on the display device to a user for selection of a protocol for an imaging task using said x-ray device.

14. The imaging system according to claim 13, wherein said x-ray device is a cone-beam computer tomograph, and the initial volumetric representation of the patient is obtained from a computer tomograph.

15. A non-transitory computer-readable medium, comprising a computer program product for carrying out the steps of the method according to claim 1 when the computer program product is loaded into a memory and executed by a data processor of the device according to claim 12.

* * * * *

UNITED STATES PATENT AND TRADEMARK OFFICE
CERTIFICATE OF CORRECTION

| | | |
|---|---|---|
| PATENT NO. | : 10,022,098 B2 | Page 1 of 1 |
| APPLICATION NO. | : 14/795206 | |
| DATED | : July 17, 2018 | |
| INVENTOR(S) | : Gerhard Kleinszig et al. | |

It is certified that error appears in the above-identified patent and that said Letters Patent is hereby corrected as shown below:

In the Specification

The following text should appear in Column 1, between Lines 4 and 5:
GOVERNMENT INTEREST
This invention was made with government support under Grant
Number EP017571, awarded by the National Institutes of Health.
The United States government has certain rights in the invention.

Signed and Sealed this
Twenty-eighth Day of August, 2018

Andrei Iancu
*Director of the United States Patent and Trademark Office*